United States Patent [19]
Klicek et al.

[11] Patent Number: 5,370,645
[45] Date of Patent: Dec. 6, 1994

[54] ELECTROSURGICAL PROCESSOR AND METHOD OF USE

[75] Inventors: Michael S. Klicek, Boulder; William G. Patterson, Longmont, both of Colo.

[73] Assignee: Valleylab Inc., Boulder, Colo.

[21] Appl. No.: 47,907

[22] Filed: Apr. 19, 1993

[51] Int. Cl.⁵ .............................................. A61B 17/39
[52] U.S. Cl. ......................................... 606/35; 606/34
[58] Field of Search ..................................... 606/32–40

[56] References Cited

U.S. PATENT DOCUMENTS

| | | |
|---|---|---|
| 3,964,487 | 6/1976 | Judson . |
| 3,980,085 | 9/1976 | Ikuno . |
| 4,092,986 | 6/1978 | Schneiderman . |
| 4,126,137 | 11/1978 | Archibald . |
| 4,188,927 | 2/1980 | Harris . |
| 4,321,926 | 3/1982 | Roge . |
| 4,372,315 | 2/1983 | Shapiro et al. . |
| 4,590,934 | 5/1986 | Malis et al. ........................... 606/37 |
| 4,658,819 | 4/1987 | Harris et al. . |
| 4,658,820 | 4/1987 | Klicek .................................. 606/37 |
| 4,727,874 | 3/1988 | Bowers et al. . |
| 5,167,658 | 12/1992 | Ensslin ................................. 606/34 |

FOREIGN PATENT DOCUMENTS

0336742  10/1989  European Pat. Off. .............. 606/34

*Primary Examiner*—Stephen C. Pellegrino
*Assistant Examiner*—Michael Peffley
*Attorney, Agent, or Firm*—Peter C. Richardson; Lawrence C. Akers; Aaron Passman

[57] ABSTRACT

A circuit, for monitoring and controlling parameters of an electrosurgical unit, ESU, relative to load and the RF energy, has a load responsive output sensing circuit that measures the ESU load. A signal modifier, attached to the sensing circuit enhances the signals measured and transmits them to a buffer. An analog to digital converter, A/D, digitize the signals and samples wave pulse train at about eight million samples per second. A data memory stores the digitized signals. A RF drive clock connects to the ESU output; a sample clock uses phase shifting to interrogate the input signals to a processor, DSP, at a greater sampling rate of frequency than without. The DSP receives the stored signals from the data memory and processes them while monitoring and calculating ESU parameters measured, i.e. voltage, current, power, load impedance, leakage current, peak to peak voltage, peak to peak current, spectral content and/or crest factor of the RF wave pulse train energy to use as controlling feedback to the either a high voltage power supply in the ESU, regulating the RF drive pulses or both. A method monitors and controls the ESU relative to load has the steps of collecting parameters with the ESU output sensing circuit responsive to loads; enhancing signals with the signal modifier; transmitting signals to the buffer; converting signals with the A/D converter; storing signals in the data memory; receiving signals in the DSP, and processing, monitoring and controlling signals by repeatedly measuring ESU output parameters.

16 Claims, 3 Drawing Sheets

ELECTROSURGICAL PROCESSOR AND METHOD OF USE

FIELD OF THE INVENTION

This invention relates to a circuit sensitive to the output energy of an electrosurgical unit which output energy must varies as a function of load, and more particularly, to the parameters which measure generator output and their regulation by converting signals thereof from analog form to digital form for evaluation by a processor with enhancement therein and thereafter controlled by a feedback loop to the generator.

BACKGROUND OF THE DISCLOSURE

An electrosurgical unit includes a radio frequency generator and its controls, which can be used for cutting or coagulating with high frequency electrical energy such as pulses shaped to enhance cutting or coagulation. Using an electrosurgical generator in a surgical procedure, it is possible for the surgeon to cut, to blend or cut with hemostasis, or to purely coagulate. The surgeon can easily select and change the different modes of operation as the surgical procedure progresses. In each mode of operation, it is important to regulate the electrical power delivered to the patient to achieve the desired surgical effect. Applying more power than necessary results in tissue destruction and prolongs healing. Applying less than the desired amount of electrical power inhibits the surgical procedure. It is desirable to control the output energy from the electrosurgical generator for the type of tissue being treated. Different types of tissues will be encountered as the surgical procedure progresses and each unique tissue requires more or less power as a function of frequently changing tissue impedance. Even the same tissue will present a different load as the tissue is desiccated and the position and size of the electrosurgical tool will effect the load. That is, the deeper the tool is moved into the tissue or the further the tool is pulled from the tissue will change the impedance or load. Accordingly, all successful types of electrosurgical generators use some form of automatic power regulation to control the electrosurgical effects desired by the surgeon.

Two conventional types of power regulation are in commercial electrosurgical generators. The most common type controls the DC power supply of the generator by limiting the amount of power provided from the AC mains to which the generator is connected. A feedback control loop compares the output voltage supplied by the power supply to a desired setting to achieve regulation. Another type of power regulation in commercial electrosurgical generators controls the gain of the high-frequency or radio frequency amplifier. An analogue feedback control loop compares the output power supplied from the RF amplifier for adjustment to a desired power level. The output is adjusted accordingly but generators commonly and currently in use do not digitally measure RF output power delivered to the load and thereafter regulate accordingly. Usually, the generators are run open loop, i.e. without feedback but if controlled, then only to a constant radio frequency output voltage.

Specifically, U.S. Pat. Nos. 3,964,487; 3,980,085; 4,188,927 and 4,092,986 have circuitry to reduce the output current in accordance with increasing load impedance. In those patents constant voltage output is maintained and the current is decreased with increasing load impedance. Similarly, U.S. Pat. No. 4,126,137 controls the power amplifier of the electrosurgical unit in accord with a non linear compensation circuit applied to a feedback signal derived from a comparison of the power level reference signal and the mathematical product of two signals including sensed current and voltage in the unit.

Known types of radio frequency power regulation have achieved moderate success but certain undesirable characteristics are associated with each. One undesirable characteristic involves the response time for regulation. The impedance of the different tissues encountered during the surgical procedure can fluctuate substantially. In moving from a high impedance tissue to a low impedance tissue, the low impedance tissue may be needless destroyed or damaged before the electrosurgical generator can reduce its output power to a level compatible with the lower impedance of the tissue. Similarly, when a high impedance tissue is encountered, the output power from the generator may be momentarily inadequate to create or continue the precise surgical effect desired by the surgeon. Wherefore, execution of the surgical procedure becomes difficult or impossible. Recognizing this problem is U.S. Pat. No. 4,658,819 wherein the power delivered to the load is a function of the voltage from a DC supply and the load as measured by sensors of load voltage and current. A microprocessor controller digitizes the sensing signals and computes the load impedance and actual power being delivered to the load. The microprocessor controller accordingly repeats the measurement, calculation and correction process approximately every 20 milliseconds as long as the generator is operating.

Another problem of radio frequency output power regulation in previous electrosurgical generators results because they have been designed to attain maximum power transfer at intermediate impedance ranges. As with amplifiers, an electrosurgical generator will achieve maximum power transfer when its internal impedance equals the output load impedance to which it is connected. At high impedances, the power delivered typically rolls off because of the difference between load impedance compared and the internal impedance. To compensate, surgeons increase the initial power setting to a level higher than necessary. Once the incision passes through the high impedance tissue, the output power setting remains too great and tissue destruction or undesirable surgical effects result. For example, the initial incision passes through skin with a relatively large percentage of dead cells, which contain considerably less moisture than other cells in tissues beneath the skin; that is, the epidermis has increased impedance compared to the impedance of the tissues therebelow. A higher power setting is required for the initial incision and thereafter a reduced amount of power will work. With commercially available electrosurgical generators, the initial incision is often deeper than desired because the active electrode, i.e., the electrosurgical instrument, cuts deeper than the surgeon desires due to the excessive energy delivery. The surgeon desires to control the depth of the incision and conduct the surgical procedure in controlled depth levels. If the power regulation is greater than needed, a deeper incision in certain areas results in undesired bleeding. For that reason most surgeons prefer to make the initial incision using a conventional scalpel, instead of using the active electrode blade of an electrosurgical generator.

Another radio frequency output power regulation related problem of available electrosurgical generators is open circuit flashing just prior to the start of the surgery. Prior to the electrosurgical procedure commencement, no output power is supplied due to the open circuit condition. The regulation circuit attempts to compensate with maximum power delivery. When the active electrode is positioned an operative distance from the tissue, an arc of relatively high voltage ensues due to the maximum power delivery capability initiated by the power regulation circuit. Continual arcing is desired in the coagulation (fulguration) mode of operation but is otherwise undesirable. The power regulation circuit eventually reduces the excessive power but the initial arcing or flash may already have caused excessive tissue destruction. The flash and excessive tissue destruction can occur anytime the surgeon moves the active electrode toward the tissue.

Open circuit or excessively high output impedance conditions increase the risks of alternate path burns to the patient. Alternate path burns occur when current flowing from the patient to some surrounding grounded conductive object, such as the surgical table, rather than returning to the electrosurgical generator through the patient return electrode. Reducing the output voltage under open circuit or high impedance conditions reduces the magnitude of and potential for radio frequency leakage currents.

Another radio frequency output power regulation related problem of commercial electrosurgical generators relates to shorting the output terminals of the generator. A frequent though not recommended, technique of quickly determining whether an electrosurgical generator is operating is to simply short the two output electrodes and observe an electrical spark. A possible result of shorting is the destruction of the power supply in the generator. The generator quickly attempts to regulate from a high power open circuit condition to a short circuit low impedance condition. Due to the limitations on regulating speed, the electrical power components of the power supply are overdriven and quickly destroyed before adequate compensation can occur.

U.S. Pat. No. 4,727,874 discloses an electrosurgical generator with a high frequency pulse width modulated feedback power control wherein each cycle of the generator is regulated in power content by modulating the width of the driving energy pulses. Instantaneous analysis of parts of the high frequency signals of the effects of impedance loads on the electrosurgical unit in real time is not possible. It is desirable to be able to examine a series of RF pulses and control the output with respect to the real time effect on tissue. Instantaneous corrections to the output are not possible; only changes over the average of the output pulses are feasible, see for example U.S. Pat. No. 4,372,315. That patent discloses a circuit which measures impedances after delivering a set number of radio frequency pulses on a pulse burst by pulse burst basis. U.S. Pat. No. 4,321,926 has a feedback system to control dosage but the impedance sensing is not on a real time basis.

Electrosurgical medical procedures require controllable and close regulation of the cutting and/or coagulating high frequency energy. The energy application must be limited to a desired surgical area in order that no damage be sustained by important structures or organs in the immediate vicinity of the cutting or coagulation. Whether cutting or coagulating, the tissue is supplied with monopolar electrosurgical energy. The tissue acts as a load which in electrical terms is considered as a variable impedance that is a function of the nature of the tissue being surgically treated. The load impedance has resistive, capacitive and inductive components and the energy pathways from the electrosurgical unit to the tissue similarly add resistive, capacitive and inductive components.

It would be preferred to instantaneously measure the variations of resistance, inductance and capacitance and correct the output of the electrosurgical unit accordingly. This, however, is impossible to do but output parameters such as voltage, current and power of the electrosurgical unit may be measured and/or calculated. Similarly, selected operational parameters such as constant current, constant voltage, and constant power can be regulated but not on an instantaneous level since the frequency of the pulses is typically 500 kilohertz. Circuits commonly in use for controlling the output of an electrosurgical unit are incapable of the response times necessary.

Analog measurement of output signals from instruments such as the electrosurgical unit are well known and in use because the physical world is primarily analog and the processing of analog signals in electronic circuits is well known and accomplished easily. For example, amplification, filtering, frequency modulation, and the like are common electronic functions of circuit designed to handle analog signals. Such signals tend to be continuous and therefore detectors of analog signals have difficulty in recognizing discontinuities in the signal brought about by change.

Digital or discreet signals are those that change from one condition to another distinct condition. For example, an "on" or an "off" condition is easily measured since there is no continuity in the change from "on" to "off". The advantage in having to deal with only two conditions, i.e. the existence of either one or the other, limits measurement and has a definite benefit since no subjective interpretation need be applied. Numerous gains are available with digitized signal including less sensitivity to change, pre-determined level of accuracy, better dynamic range, applicability to non-linear control, predictability and repeatability, insensitivity to environmental variations, replicatability, flexibility, multiplex ability and economy.

Electrosurgical units put out analog signals as their output. Processors or computers are arranged to consider digital signals and although analog to digital signals conversion is necessary, the manner in which the conversion is made bears strongly on the accuracy and ability, i.e. response time, of the circuit used.

Described herein are an electrosurgical unit control responsive to load and its method of use neither found in the literature nor practiced in the field. The literature is of interest for its teachings of the knowledge of skilled artisans at the time of this invention.

SUMMARY OF THE INVENTION

Disclosed and claimed are the electrosurgical unit control responsive to load. A circuit for monitoring operating parameters of an electrosurgical unit and for controlling those parameters relative to a load placed upon the radio frequency energy supplied by the electrosurgical unit preferably has a sensing circuit connected to the output of the electrosurgical unit and responsive to loads applied thereacross for collecting parameters indicative of the operation of the electrosurgical unit under load.

A signal modifier connected to the sensing circuit most preferably enhances parameters of the signals collected and thereafter transmits the signals to a buffer that may be located therein. An analog to digital converter, for receiving signals from the buffer, converts the analogue form of the signals into digital form. A data memory stores the signals in digitized form, and a processor connected thereto receives the stored signals. The processor is most preferably capable of processing the signals while continually monitoring and controlling the electrosurgical unit by measurement of the voltage, current, and/or power for the instantaneous calculation of energy output, load impedance, leakage current, spectral content and/or crest factor of the wave pulse train of the radio frequency energy. Other parameters may also be measured and/or calculated as desired.

The analog to digital converter is preferably of the flash type. A RF drive clock may be connected to a digital drive for the radio frequency stage of the electrosurgical unit. A feedback loop is in the preferred embodiment connected to the electrosurgical unit so a high voltage power supply therein may be manipulated. The feedback loop may alternatively be connected to the electrosurgical unit so the radio frequency drive pulses of a main control circuit of the electrosurgical unit may be regulated. The feedback loop may in an alternate arrangement be connected to the electrosurgical unit so a high voltage power supply therein may be manipulated and so the radio frequency drive pulses of a main control circuit of the electrosurgical unit may be regulated.

The output performance parameters including the constant current, constant voltage or power may be calculated as a root mean square value, monitored and/or regulated through an input of the processor. The output parameters of the electrosurgical unit may be calculated for controlling performance parameters including root mean square or peak to peak voltage, root mean square or peak to peak current, and root mean square leakage current for consideration of each as the control signal for the feedback loop of the electrosurgical unit.

In the preferred embodiment of a feedback control for an electrosurgical unit, the signals therefrom are enhanced by the processor. Sixteen MHz sampling can be accomplished with or without phase shifting the location on each pulse whereat the data is measured. Phase shifting simply permits sufficient simulation of 16 MHz sampling with less costly components. The signals obtained are split into two sets of 256 each by recording at 8 megahertz. A sample clock produces a square wave pulse train for timing data acquisition first at the rising edge and then at the falling edge of each square wave pulse of the sample clock in adjacent cycles of a particular wave pulse train of interest. For each 16 pulses of the electrosurgical unit radio frequency drive, the processor samples the output of the electrosurgical unit 16 times thereby generating 256 data points for the rising edge and an additional 256 data points for the falling edge of each square wave timing pulse of the sample clock.

Thus the signal resolution may be enhanced by the processor and the phase shifting sample clock that permit data acquisition at a frequency greater than the processor could without the phase shifting sample clock. The output of the electrosurgical unit can thereby be monitored and controlled over a broad spectral input to the electrosurgical unit rapidly enough to correct output in accordance with measured load.

A method for monitoring operating parameters of an electrosurgical unit and for controlling those parameters relative to a load placed upon the radio frequency energy supplied by the electrosurgical unit preferably includes collecting parameters indicative of the operation of the electrosurgical unit under load with a sensing circuit connected to the output of the electrosurgical unit and responsive to loads applied thereacross. The step of enhancing parameters of the signals collected with a signal modifier connected to the sensing circuit follows. Transmitting the enhanced signals to a buffer and converting the analogue form of the signals into digital form, with an analog to digital converter connected for receiving signals from the buffer, are preferably the next two steps. The added step of storing the signals in digitized form in a data memory is preferred. Receiving the stored signals from the data memory in a processor is a further step. The step of processing the signals while continually monitoring and controlling the electrosurgical unit, by measurement of the voltage, current, power, load impedance, leakage current, spectral content and/or crest factor of the wave pulse train of the radio frequency energy with the processor, completes the preferred method.

DETAILED DESCRIPTION OF THE INVENTION

A circuit for monitoring operating parameters of an electrosurgical unit 10 and for controlling those parameters relative to a load placed upon the radio frequency energy supplied by the electrosurgical unit 10 and method of use thereof are disclosed and claimed. The claims are not limited to the structure for article described and illustrated by way of example and the methods its use specifically explained. The claims are to be considered in view of the existing knowledge of skilled artisans in the Field prior to the inventions defined by the language of the claims herein as amended or considered in view of knowledge of skilled artisans prior to these inventions.

Figure 1:
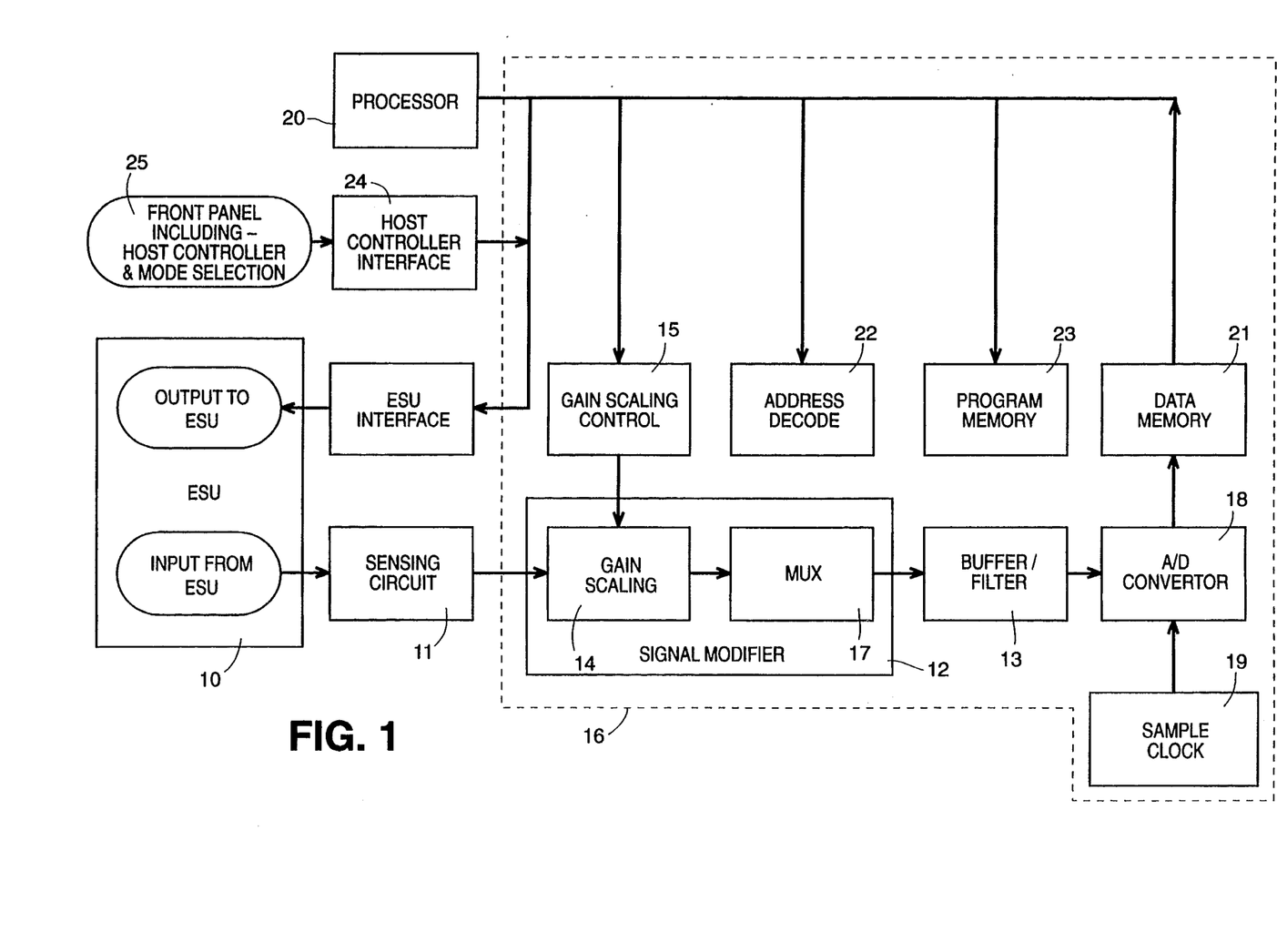
FIG. 1 is a schematic block diagram of the circuit for monitoring operating parameters of an electrosurgical unit and for controlling those parameters relative to a load placed upon the radio frequency energy supplied by the electrosurgical unit.

In FIG. 1, a schematic drawing in block form, has the circuit for monitoring operating parameters of the electrosurgical unit 10. Digital signal processing for instantaneously controlling those parameters relative to a load placed upon the radio frequency energy supplied by the electrosurgical unit 10 is in the schematic block diagram, FIG. 2.

A sensing circuit 11 is capable of collecting parameters indicative of the operation of the electrosurgical unit 10 when under load. The load being the impedance to energy applied to cut or coagulate tissue; that impedance varies and is composed of inductive, capacitive and resistive components which constitute the varying impedance load carried by the electrosurgical unit 10. The cables or wires from the electrosurgical unit 10 output to any instrument used for cutting or coagulating tissue or a blend mode thereof add an impedance component to the system and is therefore a part of the load as is the particular instrument.

In FIG. 1, a signal modifier 12 connects to the sensing circuit 11 for enhancing parameters of the signals collected and for transmitting those signals to a buffer 13 therein. The signal modifier 12 includes therein a gain scaling element 14 that adjusts or attenuates the amplitude of the signal from the sensing circuit 11. A gain scaling element control 15 sets the gain scaling element 14 and is responsive to signal processing in a feedback loop 16 as will be explained in connection with the circuit for monitoring and controlling parameters disclosed in FIG. 1.

A MUX 17 or multiplexing unit that is capable of selecting one of several signals to be measured; specifically, the more important signals are selected and transmitted to the buffer 13. The relative priority of the signals parameter selected, i.e. monopolar or bipolar voltage, current, or leakage current, is a function of the specific mode chosen by the operator. As an example, the preferred embodiment measures the voltage and current thirty two times before the leakage current is checked. The ratio of the measurement is easily set as an input to the multiplexing unit 17.

The buffer 13 receives the selected and multiplexed signals from the multiplexing unit 17 to condition those signal for use as input to the analog to digital converter 18. A sample clock 19 establishes the frequency of sampling and is connected to the analogue to digital converter 18. The buffer 13 is an amplifier in parallel with a resistance such that the signal level is compatible with the particular analog to digital converter 18.

As an example, the high frequency output is in the range of 500 kilohertz and voltage samples taken by the sensing circuit 11. The sensing circuit 11 provides instantaneous values of current and voltage instantaneously from the secondary side of the ESU 10 output transformer. The average values, in digitized form, are supplied to a processor 20 which calculates the root mean square (RMS) of the wave pulse train of the high frequency output. Under different mode settings, the gain scaling element 14 is consistent with the mode selected and adjusts the consideration of the high frequency output signal to the area on the wave pulse train of greatest interest.

The assignee of this application owns U.S. Pat. No. 4,658,819 on RMS electrosurgical unit 10 control. The sensing circuit 11 considers a wave pulse train with a frequency of eight million data points per second and 256 samples are taken which in view of the speed represents sixteen complete sine waves. This concerns how the measurements of such high frequency wave pulse train are accomplished accurately. The RMS value of $$y_{RMS} = \left( 1/N \sum_{N=0}^{N} (y_n)^2 \right)^{\frac{1}{2}}$$

wherein voltage samples are taken 256 times during the sixteen complete sine wave pulse train. The peak to peak voltage change or difference is approximately twice the RMS voltage times a predefined crest factor. If the power output is assumed to be constant and the power desired has been selected by the operator, then the RMS values for voltage and current can be instantaneously calculated. Consequently, the RMS power as measured from the sampling of the wave pulse train is: $P_{RMS} = V_{RMS} \times I_{RMS}$. The load impedance as measured at the secondary side of the transformer by the sensing circuit 11 is: $Z = V_{RMS}/I_{RMS}$ and that can be used to establish a control voltage for use in adjusting the output of the electrosurgical unit 10. The processor 20 is programmed to receive the instantaneous wave pulse train samplings and by calculation convert them into an equivalent control voltage ($E_{con}$) that adjusts the electrosurgical unit 10, that is to say that, the $E_{con}$ is a signal to operate the high voltage direct current HVDC of the electrosurgical unit 10.

For example, when the $P_{RMS} > P_{DESIRED}$, then $E_{con} = E_{con} - 1$. Conversely, $E_{con} = E_{con} + 1$ when $P_{RMS} < P_{DESIRED}$. If $E_{con} > E_{con\ max}$ then the programmed processor 20 makes $E_{con} = E_{con\ max}$ and conversely when $E_{con} < E_{con\ min}$, the $E_{con} = E_{con\ min}$. Similarly, when $I_{Lkg\text{-}RMS} > I_{Lkg\text{-}max}$, then $E_{con} = E_{con} - 1$. Should the sample signals saturate the analog to digital converter 18, then $E_{con} = E_{con}`1$. If load impedance $Z > $ open circuit, the $E_{con} = E_{con\ open\ circuit}$.

Figure 3:
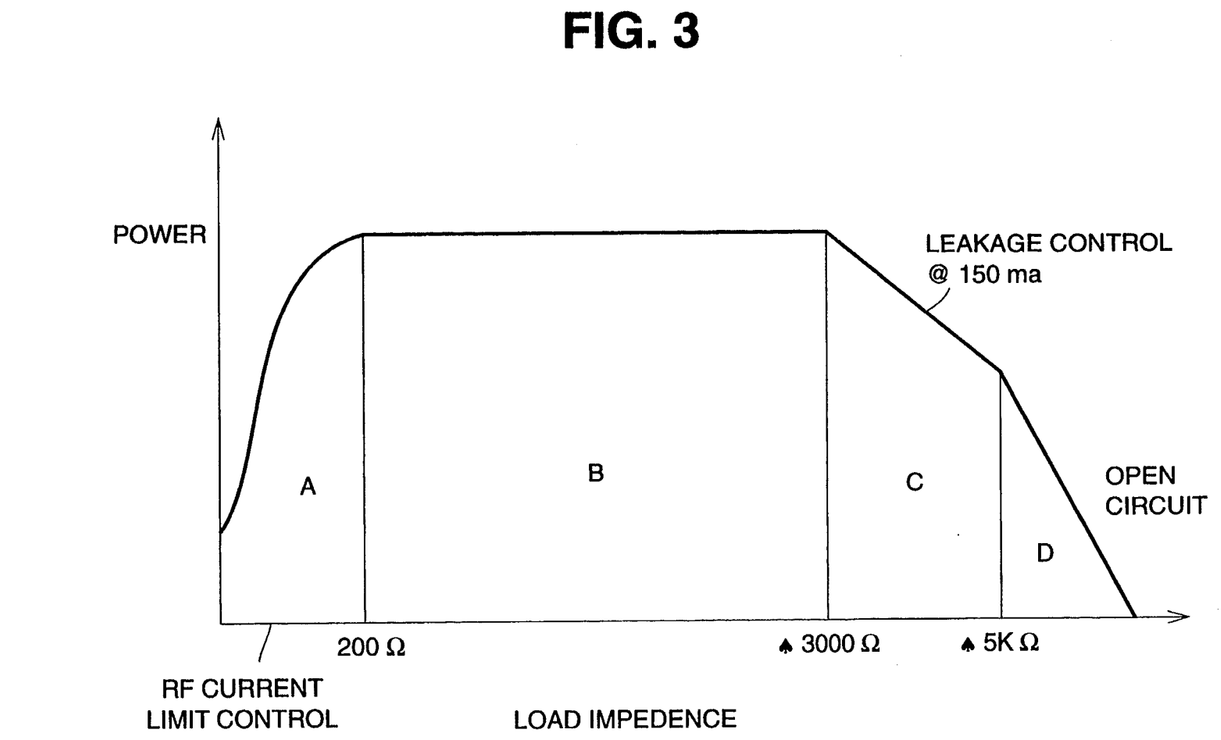
FIG. 3 is a plot of the power (y axis) verses load impedance (x axis).

In FIG. 3 a plot of the power (y axis) verses load impedance (x axis) is shown. The control of the output power to be substantially constant is performed in segments labelled A, B, C, D which are related to the situations discussed in the preceding paragraph. That is to say that in FIG. 3 the A segment of the power curve is up to about 200 ohms of impedance and is essentially flat at about 50 watts; the power set by the operator. The B segment is also constant at the prescribed power level until leakage control is initiated because the difference in output and return current is more than 150 milliamperes. Under that condition the curve shown for segment C has the power reduced with increasing impedance. Finally segment D illustrates open circuit conditions wherein the impedance is greater and the reduction in power faster.

Another way to relate the segments to the processor 20 control is segment A when the $P_{RMS} > P_{DESIRED}$, then $E_{con} = E_{con} - 1$ and conversely, $E_{con} = E_{con} + 1$ when $P_{RMS} < P_{DESIRED}$. Segment B when the $P_{RMS} > P_{DESIRED}$, then $E_{con} = E_{con} - 1$ and conversely, $E_{con} = E_{con} + 1$ when $P_{RMS} < P_{DESIRED}$ is $E_{con} > E_{con\ max}$ so that the programmed processor 20 makes $E_{con} = E_{con\ max}$ and conversely when $E_{con} < E_{con\ min}$, the $E_{con} = E_{con\ min}$. Segment C is $I_{Lkg\text{-}RMS} > I_{Lkg\text{-}max}$, so that $E_{con} = E_{con} - 1$. Should the sample signals saturate the analog to digital converter 18, then $E_{con} = E_{con} - 1$. When the load impedance $Z > Z_{open\ circuit}$, the $E_{con} = E_{con\ open\ circuit}$ for segment D.

The signal modifier 12 connects to an analog to digital converter 18 so that signals from the buffer 13 in the signal modifier 12 may be converted from analog form into digital form. The digitized signals are such that their existence or nonexistence are provided to a data memory 21 for storing the signals defining the parameters of operation in digitized form until they are used by a processor 20 connected thereto.

The processor 20 is capable of processing the signals while continually monitoring and controlling the electrosurgical unit 10. Associated with the processor 20 which is preferably an integrated circuit, e.g. Analog Devices ADSP 2105, there is an address decoder 22 which receives the signals from the processor 20. The address decoder 22 enables various output registers by presenting the address thereof since the address of any component in the system is known to the address decoder 22. A program memory 23 in the processor 20 provides instruction in accordance with the need to measure the voltage, current, power, load impedance, leakage current, spectral content and/or crest factor of the wave pulse train of the radio frequency energy as desired. A digital signal processing data ram buffer 13 in the digital processor 20 first receives the stored signals from the data memory 21 for use in the digital signal processing.

Shown also in FIG. 1 are system controls identified as a host controller interface 24 which conveys information from a front panel 25, i.e. power, mode, etc. to the processor 20. These enumerated blocks operate together enabling the user and providing the following functions: (1) selection of desired power, (2) selection of mode, (3) selection of control scheme.

Figure 2:
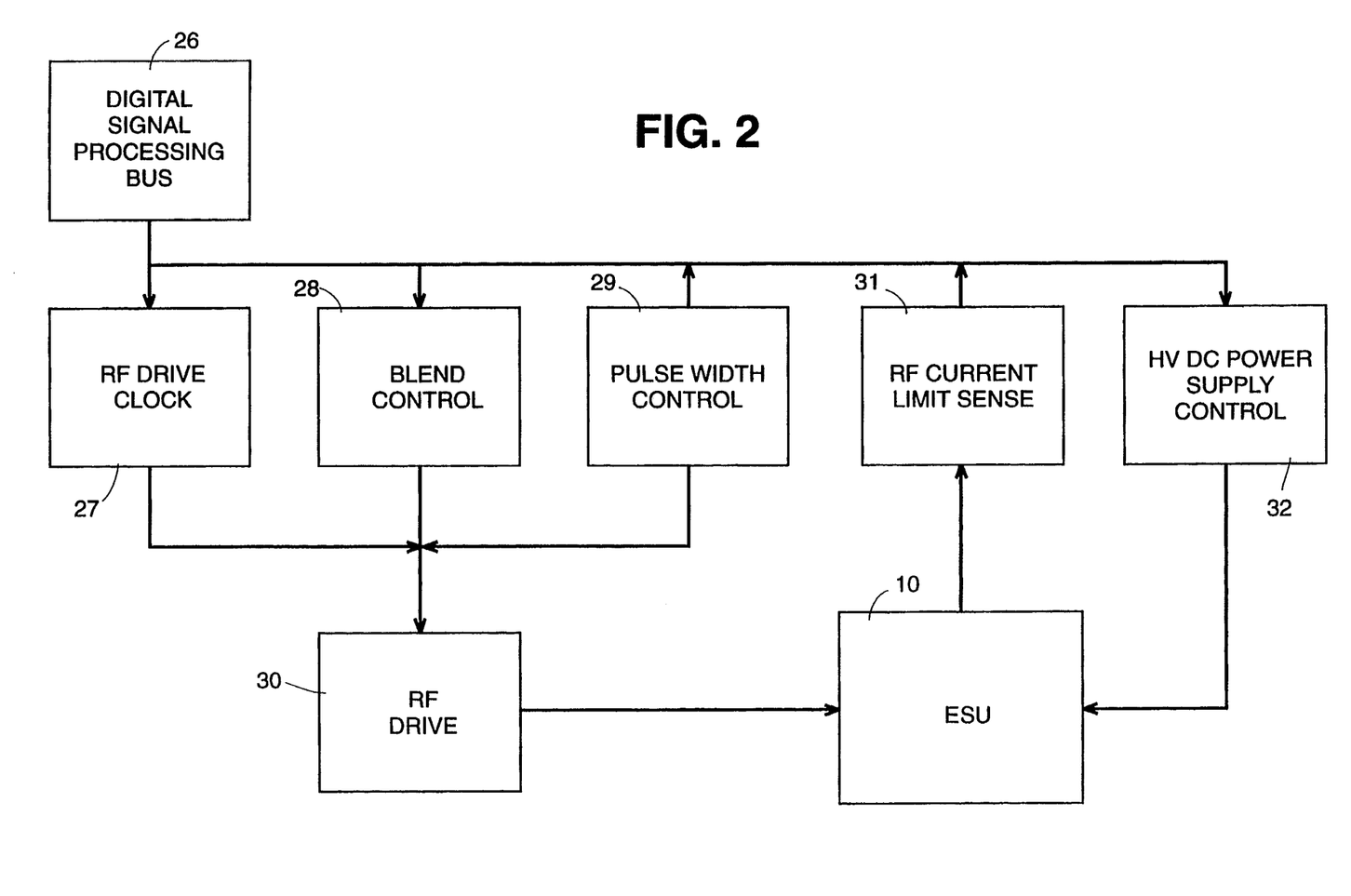
FIG. 2 is a schematic block diagram of the circuit for the processor bus and radio frequency drive of an electrosurgical unit.

It will be noted in FIG. 1 that the resulting output from the circuit for monitoring and controlling parameters is sent therefrom to a digital signal processing bus 26 which is disclosed in FIG. 2 wherein the digital signal processing bus 26 includes an RF drive clock 27, a blend control 28 and a pulse width control 29 to receive the signals from the circuit for monitoring, operating parameters and controlling those parameters of FIG. 1. The RF drive clock 27, the blend control 28, and the pulse width control 29 each modify time and construct the signals received by the digital signal processor bus 26 so that those may be fed into a radio frequency drive 30 for the electrosurgical unit 10 generator. The RF drive clock 27 determines the basic RF output frequency. The blend control 28 alternately passes and blocks groups of pulses for blend and coagulation operating modes. The pulse width control 29 limits the width of individual RF drive pulses for controlling the radio frequency output signal, by means other than by controlling the high voltage power supply or the gain of the radio frequency amplifier.

The digital signal processing bus 26 also receives a signal from the electrosurgical unit 10 which indicates the radio frequency output stage of the electrosurgical unit 10 RF current limit 31 is nearing its safe operating limit. The current limit 31 as set by the manufacturer of the unit, i.e. for the Valleylab Force 40 the current limit 31 varies by mode power etc. If that condition occurs, the drive of the electrosurgical unit 10 (econ or pulse width) is reduced until the hardware limit ceases. This is done either by reducing the control voltage (econ) to the HVDC or by pulse width change to the RF drive clock 27.

The signal from the digital signal processor bus 26 is also supplied to a DC supply control 32 which uses that signal to regulate the high voltage direct current (HVDC) power supply in the electrosurgical unit 10. Econ is an analog control voltage applied to an input of the electrosurgical unit 10 power supply. The output voltage of the power supply is proportional to econ; for example, if econ is approximately 5 volts then output voltage is approximately 200 volts and when econ is approximately 1 volt then output voltage is approximately 40 volts. In addition, the processor 20 signal as modified by the RF current limit 31 sensor is used as a radio frequency current limit 31 control input which is capable of providing a current control for the electrosurgical unit 10 as already explained.

The analog to digital converter 18 is of the flash type and thus capable of sampling wave pulse train at about eight million samples per second. An analog to digital converter of this type may be obtained from Motorola part number MC10319. Consequently, the wave pulse train is sampled periodically and several times during, for example, a cycle or some cycles. Phase shifting can be used as explained to enable the application of less costly components with the same high frequency response. That is to say that, the high frequency resolution is doubled without the expense of more costly components.

The electrosurgical unit 10 has a high voltage power supply therein which is manipulated by the feedback loop 16. The feedback loop 16 is connected to the electrosurgical unit 10 so that radio frequency drive 30 pulses of a main control circuit of the electrosurgical unit 10 can be regulated. The feedback loop 16 is accordingly capable of regulating the electrosurgical unit 10 by either adjusting the RF output by control of the electrosurgical unit 10 high voltage power supply, by control of the RF drive pulses, or by a combination of both. The output performance parameters of the electrosurgical unit 10 include constant current, constant voltage, or power and those may be calculated as a root mean square value, may be monitored and/or may be regulated through input of those signals into the processor 20. The output parameters of the electrosurgical unit 10 may, after calculation, be used for controlling the performance parameters of the electrosurgical unit 10. Those performance parameters include for example, peak-to-peak voltage, peak-to-peak current, and leakage current. Each of those performance parameters are useful independently or in combination as a control signal in the feedback loop 16 to the electrosurgical unit 10.

The signals applied to the analog to digital signal conversion can be sampled at 8 megahertz. Consequently, for each pulse of the electrosurgical unit 10 radio frequency drive 30, the processor 20 is capable of sampling the output of the electrosurgical unit 10 sixteen times. The signal resolution is the same as if sampled at 16 MHz since the acquisition of data at the rising edge and falling edge of each square wave pulse of the sample clock is consequently permitted at that greater frequency. The analog to digital conversion allows the output of the electrosurgical unit 10 to be monitored and controlled over a broad spectral input to the electrosurgical unit 10 at a speed rapid enough to correct the input in accordance with the measured load and without undue delay.

What is claimed is:

1. A circuit for monitoring operating parameters of an electrosurgical unit with an output transformer having primary and secondary windings and for controlling in real time those parameters relative to a load placed upon the radio frequency energy supplied by the electrosurgical unit, comprising:

a sensing circuit means connected to receive radio frequency energy supplied by the output of the electrosurgical unit and responsive to loads applied across the radio frequency energy supplied, the sensing circuit means connected for providing instantaneous values of current and voltage from the secondary windings so the sensing circuit means collects parameters indicative of the operation of the electrosurgical unit under load;

a signal modifier connected to the sensing circuit means, the signal modifier including enhancement means to adjust or attenuate the amplitude of the parameters from the sensing circuit means in response to signal processing and feedback;

a buffer connected to the signal modifier for receiving the enhanced parameters collected to set the level thereof;

a flash type analog to digital converter connected to the buffer for receiving signals therefrom and converting the analog form of those signals into digital form multiple times during a cycle, the flash type analog to digital converter capable of sampling wave pulse train output periodically and several times during a cycle or some cycles;

a data memory connected to the analog to digital converter for storing the converted signals in their digitized form, and a processor connected to the data memory so as receive the stored signals from the data memory, the processor connected to the electrosurgical unit and capable of processing the stored signals while continually monitoring the electrosurgical unit by measurement of the voltage, current, power, load impedance, leakage current, spectral content and/or crest factor of the wave pulse train of the radio frequency energy and then controlling the electrosurgical unit to achieve a predefined voltage, current, power, load impedance, leakage current, spectral content and/or crest factor of the wave pulse train of the radio frequency energy in accord with a mode setting and an algorithm in the processor.

2. The circuit for monitoring and for controlling of claim 1 wherein the flash type analog to digital converter is capable of sampling wave pulse train at about eight million samples per second.

3. The circuit of claim 2 wherein a sample clock means is in circuit with the flash type analog to converter so as to set the timing for storing converted signals into the data memory so the number of samples taken times the sample frequency is an integral number of RF cycle times and a RF drive clock means is in circuit with, connected to the electrosurgical unit output and the flash type analog to digital converter so as to synchronize the sample clock means of the flash type analog to digital converter with output of the electrosurgical unit.

4. The circuit of claim 3 wherein a feedback loop connecting the processor to the electrosurgical unit and the feedback loop regulates the electrosurgical unit by control of pulses of the RF drive clock means.

5. The circuit of claim 3 wherein the electrosurgical unit has a high voltage power supply associated with the electrosurgical unit and a feedback loop connecting the processor to the electrosurgical unit for manipulating and adjusting the electrosurgical unit RF output by control of the electrosurgical unit high voltage power supply and the feedback loop regulates the electrosurgical unit by control of pulses of the RF drive clock means.

6. The circuit of claim 5 wherein the processor and feedback loop are connected to control performance parameters of the electrosurgical unit including peak to peak voltage, peak to peak current, and leakage current and considers each as the control signal for the feedback loop of the electrosurgical unit.

7. The circuit of claim 3 wherein the sample clock means connected the flash type analog to digital converter and synchronized with the wave form of the electrosurgical unit output defines a square wave having rising edges and falling edges for thereby taking 16 output wave form amplitude measurements timed with each rising edge and across 16 cycles of the output wave form so 256 data points are in the data memory and in the next 16 substantially adjacent output cycles taking 16 output waveform amplitude measurements in each timed with each falling edge of each square wave pulse to merge with those in the data memory to double the number of amplitude reading of the monitored waveform for enhanced resolution.

8. The circuit of claim 1 wherein the electrosurgical unit has a high voltage power supply associated with the electrosurgical unit and a feedback loop connecting the processor to the electrosurgical unit for manipulating and adjusting the electrosurgical unit RF output by control of the electrosurgical unit high voltage power supply.

9. The circuit of claim 1 wherein an input of the processor monitors, calculates and regulates the electrosurgical unit output performance parameters received from the data memory including the constant current, constant voltage or power as a root mean square value.

10. The circuit of claim 1 wherein the processor connected to the data memory enhances the resolution of the converted signals and a phase shifting sample clock means permits signal handling at a frequency greater than the processor could handle converted signals without the sample clock means phase shifting so that the instantaneous values of current and voltage of the electrosurgical unit can be monitored and controlled to correct the transformer output thereof in real time in accord with measured load.

11. A circuit for monitoring operating parameters of an electrosurgical unit with an output transformer having primary and secondary windings and for controlling in real time those parameters relative to a load placed upon the radio frequency energy supplied by the electrosurgical unit, comprising:

a sensing circuit means connected to receive radio frequency energy supplied by the output of the electrosurgical unit and responsive to loads applied across the radio frequency energy supplied, the sensing circuit means connected for providing instantaneous values of current and voltage from the secondary windings so the sensing circuit means collects parameters indicative of the operation of the electrosurgical unit under load;

a signal modifier connected to the sensing circuit means the signal modifier including enhancement means to adjust or attenuate the amplitude of the parameters from the sensing circuit means in response to signal processing and feedback;

a buffer connected to the signal modifier for receiving the enhanced parameters collected to set the level thereof;

a flash type analog to digital converter connected to the buffer for receiving signals therefrom and converting the analog form of those signals into digital form multiple times during a cycle, the flash type analog to digital converter capable of sampling wave pulse train output periodically and several times during a cycle or some cycles at millions of samples per second;

a data memory connected to the analog to digital converter for storing the converted signals in their digitized form, and a sample clock means is in circuit with the flash type analog to digital converter so as to set the timing for storing converted signals into the data memory so the number of samples taken times the sample frequency is an integral number of RF cycle times;

a RF drive clock means is in circuit with, connected to the electrosurgical unit output and the flash type analog to digital converter so as to synchronize the sample clock means of the flash type analog to digital converter with output of the electrosurgical unit;

a processor connected to the data memory so as receive the stored signals from the data memory, the processor connected to the electrosurgical unit and capable of processing the signals while continually monitoring the electrosurgical unit by measurement of the voltage, current, power, load impedance, leakage current, spectral content and/or crest factor of the wave pulse train of the radio frequency energy and then controlling the electrosurgical unit to achieve a predefined voltage, current, power, load impedance, leakage current, spectral content and/or crest factor of the wave pulse train of the radio frequency energy in accord with a mode setting and an algorithm in the processor so the output parameters of the electrosurgical unit may be calculated for controlling performance parameters including peak to peak voltage, peak to peak current, and leakage current for consideration of each as the control signal for feedback into the electrosurgical unit;

the sample clock means for permitting measurement handling at a frequency greater than the processor could without the sample clock means so that the instantaneous values of current and voltage of the electrosurgical unit can be monitored and controlled over its broad spectral input to correct in real time the output in accordance with measured load, and a feedback loop connected to the electrosurgical unit so a high voltage power supply therein may be manipulated and so the radio frequency drive pulses of a main control circuit of the electrosurgical unit may be regulated and wherein the transformer output performance parameters including the constant current, constant voltage or power may be calculated as a root mean square value, monitored and/or regulated through an input of the processor.

12. The circuit of claim 11 wherein the stored signals from the data memory received by the processor are split into two sets of 256 each with the sample clock means by phase shifting for receiving the converted signals in the form of square wave pulse train from the analog to digital converter and the processor reads the square wave pulse train at 8 megahertz at a rising edge and a falling edge of each square wave pulse of the sample clock means in adjacent cycles.

13. The circuit of claim 11 wherein for each 16 pulses of the electrosurgical unit radio frequency drive the processor is connected to the electrosurgical unit and samples the output of the electrosurgical unit 16 times thereby generating 256 data points read at a rising edge and then subsequently another 256 at a falling edge of each square wave pulse of the sample clock means in substantially adjacent cycles.

14. A method for monitoring operating parameters of an electrosurgical unit and for controlling those parameters relative to a load placed upon the radio frequency energy supplied by the electrosurgical unit, having the steps comprising:

collecting parameters indicative of the operation of the electrosurgical unit under load with a sensing circuit means connected to receive radio frequency energy supplied by the output of the electrosurgical unit and responsive to loads applied thereacross;

enhancing parameters of the signals collected with a signal modifier connected to the sensing circuit means;

converting the analog form of the signals into digital form with an analog to digital converter connected for receiving signals from the signal modifier;

storing the signals in digitized form in a data memory for transmission therefrom to a processor;

receiving the stored signals from the data memory in the processor, and processing the signals while continually monitoring and controlling the electrosurgical unit by measurement of the voltage, current, power, load impedance, leakage current, spectral content and/or crest factor of the wave pulse train of the radio frequency energy with the processor.

15. The method for monitoring operating parameters of claim 14 wherein the step of processing the signals while continually monitoring and controlling the electrosurgical unit includes shifting the timing for obtaining signals for adjacent cycles.

16. A circuit for monitoring operating parameters of an electrosurgical unit with an output transformer having primary and secondary windings and for controlling in real time those parameters relative to a load placed upon the radio frequency energy supplied by the electrosurgical unit, comprising:

a sensing circuit means connected to receive radio frequency energy supplied by the output of the electrosurgical unit and responsive to loads applied across the radio frequency energy supplied, the sensing circuit means connected for providing instantaneous values of current and voltage from the secondary windings so the sensing circuit means collects parameters indicative of the operation of the electrosurgical unit under load;

a signal modifier connected to the sensing circuit means, the signal modifier including enhancement means to adjust or attenuate the amplitude of the parameters from the sensing circuit means in response to signal processing and feedback;

a buffer connected to the signal modifier for receiving the enhanced parameters collected to set the level thereof;

a flash type analog to digital converter connected to the buffer for receiving signals therefrom and converting the analog form of those signals into digital form multiple times during a cycle, the flash type analog to digital converter capable of sampling wave pulse train output periodically and several times during a cycle or some cycles;

a data memory connected to the analog to digital converter for storing the converted signals in their digitized form;

a processor connected to the data memory so as to receive the stored signals from the data memory, the processor connected to the electrosurgical unit and capable of processing the stored signals while continually monitoring the electrosurgical unit by measurement of the voltage, current, power, load impedance, leakage current, spectral content and/or crest factor of the wave pulse train of the radio frequency energy and then controlling the electrosurgical unit to achieve a predefined voltage, current, power, load impedance, leakage current, spectral content and/or crest factor of the wave pulse train of the radio frequency energy, the processor for controlling the electrosurgical unit in accord with the measurements, and.

a sample clock means is in circuit with the flash type analog to digital converter so as to set the timing for storing converted signals into the data memory so the number of samples taken times the sample frequency is an integral number of RF cycle times, and a RF drive clock means is in circuit with, connected to the electrosurgical unit output and the flash type analog to digital converter so as to synchronize the sample clock means of the flash type analog to digital converter with output of the electrosurgical unit.

* * * * *